US008226546B2

(12) United States Patent
Belson

(10) Patent No.: US 8,226,546 B2
(45) Date of Patent: Jul. 24, 2012

(54) STEERABLE ENDOSCOPE AND IMPROVED METHOD OF INSERTION

(75) Inventor: Amir Belson, Cupertino, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1730 days.

(21) Appl. No.: 11/129,093

(22) Filed: May 13, 2005

(65) Prior Publication Data

US 2005/0209509 A1   Sep. 22, 2005

Related U.S. Application Data

(63) Continuation of application No. 10/229,189, filed on Aug. 26, 2002, now Pat. No. 7,044,907, which is a continuation of application No. 09/790,204, filed on Feb. 20, 2001, now Pat. No. 6,468,203.

(60) Provisional application No. 60/194,140, filed on Apr. 3, 2000.

(51) Int. Cl.
A61B 1/00 (2006.01)

(52) U.S. Cl. ......... 600/114; 600/141; 600/146; 600/152

(58) Field of Classification Search .......... 600/114–118, 600/146–152; 348/65–74
See application file for complete search history.

(56) References Cited

U.S. PATENT DOCUMENTS

| | | |
|---|---|---|
| 616,672 A | 12/1898 | Kelling |
| 2,510,198 A | 6/1950 | Tesmer |
| 2,533,494 A | 12/1950 | Mitchell, Jr. |
| 2,767,705 A | 10/1956 | Moore |
| 3,060,972 A | 10/1962 | Sheldon |
| 3,096,962 A | 7/1963 | Meijs |
| 3,162,214 A | 12/1964 | Bazinet, Jr. |
| 3,168,274 A | 2/1965 | Street |
| 3,430,662 A | 3/1969 | Guarnaschelli |
| 3,546,961 A | 12/1970 | Marton |
| 3,610,231 A | 10/1971 | Takahashi |
| 3,643,653 A | 2/1972 | Takahashi et al. |
| 3,739,770 A | 6/1973 | Mori |

(Continued)

FOREIGN PATENT DOCUMENTS

DE   2823025 C2   2/1986

(Continued)

OTHER PUBLICATIONS

Hasson, H.M., "Technique of Open Laparoscopy", (from step 1 to step 9), May 1979, 2424 North Clark Street, Chicago, Illinois 60614, 3 pages.

(Continued)

*Primary Examiner* — Matthew J Kasztejna

(57) ABSTRACT

A steerable endoscope has an elongated body with a selectively steerable distal portion and an automatically controlled proximal portion. The endoscope body is inserted into a patient and the selectively steerable distal portion is used to select a desired path within the patient's body. When the endoscope body is advanced, an electronic motion controller operates the automatically controlled proximal portion to assume the selected curve of the selectively steerable distal portion. Another desired path is selected with the selectively steerable distal portion and the endoscope body is advanced again. As the endoscope body is further advanced, the selected curves propagate proximally along the endoscope body, and when the endoscope body is withdrawn proximally, the selected curves propagate distally along the endoscope body. This creates a serpentine motion in the endoscope body that allows it to negotiate tortuous curves along a desired path through, around, and between organs within the body.

20 Claims, 6 Drawing Sheets

U.S. PATENT DOCUMENTS

| | | |
|---|---|---|
| 3,773,034 A | 11/1973 | Burns et al. |
| 3,858,578 A | 1/1975 | Milo |
| 3,897,775 A | 8/1975 | Furihata |
| 3,913,565 A | 10/1975 | Kawahara |
| 3,946,727 A | 3/1976 | Okada |
| 4,054,128 A | 10/1977 | Seufert |
| 4,176,662 A | 12/1979 | Frazer |
| 4,236,509 A | 12/1980 | Takahashi |
| 4,240,435 A | 12/1980 | Yazawa et al. |
| 4,273,111 A | 6/1981 | Tsukaya |
| 4,327,711 A | 5/1982 | Takagi |
| 4,366,810 A | 1/1983 | Slanetz, Jr. |
| 4,432,349 A | 2/1984 | Oshiro |
| 4,499,895 A | 2/1985 | Takayama |
| 4,503,842 A | 3/1985 | Takayama |
| 4,543,090 A | 9/1985 | McCoy |
| 4,559,928 A | 12/1985 | Takayama |
| 4,577,621 A | 3/1986 | Patel |
| 4,592,341 A | 6/1986 | Omagari et al. |
| 4,601,283 A | 7/1986 | Chikama |
| 4,621,618 A | 11/1986 | Omagari |
| 4,624,243 A | 11/1986 | Lowery et al. |
| 4,630,649 A | 12/1986 | Oku |
| 4,646,722 A | 3/1987 | Silverstein et al. |
| 4,648,733 A | 3/1987 | Merkt |
| 4,651,718 A | 3/1987 | Collins et al. |
| 4,655,257 A | 4/1987 | Iwashita |
| 4,686,963 A | 8/1987 | Cohen et al. |
| 4,753,223 A | 6/1988 | Bremer |
| 4,788,967 A | 12/1988 | Ueda |
| 4,793,326 A | 12/1988 | Shishido |
| 4,796,607 A | 1/1989 | Allred, III |
| 4,799,474 A | 1/1989 | Ueda |
| 4,815,450 A | 3/1989 | Patel |
| 4,832,473 A | 5/1989 | Ueda |
| 4,834,068 A | 5/1989 | Gottesman |
| 4,873,965 A | 10/1989 | Danieli |
| 4,873,990 A | 10/1989 | Holmes et al. |
| 4,879,991 A | 11/1989 | Ogiu |
| 4,884,557 A | 12/1989 | Takehana et al. |
| 4,890,602 A | 1/1990 | Hake |
| 4,895,431 A | 1/1990 | Tsujiuchi et al. |
| 4,899,731 A | 2/1990 | Takayama et al. |
| 4,904,048 A | 2/1990 | Sogawa et al. |
| 4,930,494 A | 6/1990 | Takehana et al. |
| 4,949,927 A | 8/1990 | Madocks et al. |
| 4,957,486 A | 9/1990 | Davis |
| 4,969,709 A | 11/1990 | Sogawa et al. |
| 4,971,035 A | 11/1990 | Ito |
| 4,977,887 A | 12/1990 | Gouda |
| 4,987,314 A | 1/1991 | Gotanda |
| 5,018,509 A | 5/1991 | Suzuki et al. |
| 5,060,632 A | 10/1991 | Hibino et al. |
| 5,092,901 A | 3/1992 | Hunter et al. |
| 5,125,395 A | 6/1992 | Adair |
| 5,127,393 A | 7/1992 | McFarlin et al. |
| 5,159,446 A | 10/1992 | Hibino et al. |
| 5,174,276 A | 12/1992 | Crockard |
| 5,174,277 A | 12/1992 | Matsumaru |
| 5,188,111 A | 2/1993 | Yates et al. |
| 5,217,001 A | 6/1993 | Nakao et al. |
| 5,220,911 A | 6/1993 | Tamura |
| 5,243,967 A | 9/1993 | Hibino |
| 5,251,611 A | 10/1993 | Zehel et al. |
| 5,257,617 A | 11/1993 | Takahashi |
| 5,271,381 A | 12/1993 | Ailinger et al. |
| 5,325,845 A | 7/1994 | Adair |
| 5,337,732 A | 8/1994 | Grundfest et al. |
| 5,337,733 A | 8/1994 | Bauerfeind |
| 5,347,987 A * | 9/1994 | Feldstein et al. .............. 600/109 |
| 5,348,259 A | 9/1994 | Blanco et al. |
| 5,370,108 A | 12/1994 | Miura et al. |
| 5,383,852 A | 1/1995 | Stevens-Wright |
| 5,389,222 A | 2/1995 | Shahinpoor |
| 5,394,864 A | 3/1995 | Kobayashi et al. |
| 5,400,769 A | 3/1995 | Tanii et al. |
| 5,402,768 A | 4/1995 | Adair |
| 5,429,118 A | 7/1995 | Cole et al. |
| 5,460,166 A | 10/1995 | Yabe et al. |
| 5,460,168 A | 10/1995 | Masubuchi et al. |
| 5,469,840 A | 11/1995 | Tanii et al. |
| 5,482,029 A | 1/1996 | Sekiguchi et al. |
| 5,487,757 A | 1/1996 | Truckai et al. |
| 5,507,717 A | 4/1996 | Kura et al. |
| 5,531,664 A | 7/1996 | Adachi et al. |
| 5,551,945 A | 9/1996 | Yabe et al. |
| 5,558,619 A | 9/1996 | Kami et al. |
| 5,558,665 A | 9/1996 | Kieturakis |
| 5,577,992 A | 11/1996 | Chiba et al. |
| 5,620,408 A | 4/1997 | Vennes et al. |
| 5,624,380 A | 4/1997 | Takayama et al. |
| 5,624,381 A | 4/1997 | Kieturakis |
| 5,626,553 A | 5/1997 | Frassica et al. |
| 5,645,520 A | 7/1997 | Nakamura et al. |
| 5,658,238 A | 8/1997 | Suzuki et al. |
| 5,662,587 A | 9/1997 | Grundfest et al. |
| 5,665,050 A | 9/1997 | Benecke |
| 5,667,476 A | 9/1997 | Frassica et al. |
| 5,679,216 A | 10/1997 | Takayama et al. |
| 5,728,044 A | 3/1998 | Shan |
| 5,733,245 A | 3/1998 | Kawano |
| 5,749,828 A | 5/1998 | Solomon et al. |
| 5,752,912 A | 5/1998 | Takahashi et al. |
| 5,759,151 A | 6/1998 | Sturges |
| 5,779,624 A | 7/1998 | Chang |
| 5,807,241 A | 9/1998 | Heimberger |
| 5,810,715 A | 9/1998 | Moriyama |
| 5,842,973 A | 12/1998 | Bullard |
| 5,860,914 A | 1/1999 | Chiba et al. |
| 5,876,329 A | 3/1999 | Harhen |
| 5,876,373 A | 3/1999 | Giba et al. |
| 5,885,208 A | 3/1999 | Moriyama |
| 5,897,417 A | 4/1999 | Grey |
| 5,897,488 A | 4/1999 | Ueda |
| 5,902,254 A | 5/1999 | Magram |
| 5,906,591 A | 5/1999 | Dario et al. |
| 5,908,381 A | 6/1999 | Aznoian et al. |
| 5,916,147 A | 6/1999 | Boury |
| 5,921,915 A | 7/1999 | Aznoian et al. |
| 5,928,136 A | 7/1999 | Barry |
| 5,941,815 A | 8/1999 | Chang |
| 5,957,833 A | 9/1999 | Shan |
| 5,976,074 A | 11/1999 | Moriyama |
| 5,989,182 A | 11/1999 | Hori et al. |
| 5,989,230 A | 11/1999 | Frassica |
| 5,993,381 A | 11/1999 | Ito |
| 5,996,346 A | 12/1999 | Maynard |
| 6,036,636 A | 3/2000 | Motoki et al. |
| 6,042,155 A | 3/2000 | Lockwood |
| 6,048,307 A | 4/2000 | Grundl et al. |
| 6,066,132 A | 5/2000 | Chen et al. |
| 6,099,464 A | 8/2000 | Shimizu et al. |
| 6,099,485 A | 8/2000 | Patterson |
| 6,106,510 A | 8/2000 | Lunn et al. |
| 6,149,581 A | 11/2000 | Klingenstein |
| 6,162,171 A | 12/2000 | Ng |
| 6,174,280 B1 | 1/2001 | Oneda |
| 6,179,776 B1 | 1/2001 | Adams |
| 6,210,337 B1 | 4/2001 | Dunham et al. |
| 6,221,006 B1 | 4/2001 | Dubrul et al. |
| 6,249,076 B1 | 6/2001 | Madden et al. |
| 6,270,453 B1 | 8/2001 | Sakai |
| 6,306,081 B1 | 10/2001 | Ishikawa et al. |
| 6,309,346 B1 | 10/2001 | Farhadi |
| 6,315,714 B1 | 11/2001 | Akiba |
| 6,327,492 B1 | 12/2001 | Lemelson |
| 6,402,687 B1 | 6/2002 | Ouchi |
| 6,408,889 B1 | 6/2002 | Komachi |
| 6,468,203 B2 | 10/2002 | Belson |
| 6,482,149 B1 | 11/2002 | Torii |
| 6,527,706 B2 | 3/2003 | Ide |
| 6,554,793 B1 | 4/2003 | Pauker et al. |
| 6,610,007 B2 | 8/2003 | Belson et al. |
| 6,616,600 B2 | 9/2003 | Pauker |
| 6,638,213 B2 | 10/2003 | Ogura et al. |
| 6,641,528 B2 | 11/2003 | Torii |
| 6,699,183 B1 | 3/2004 | Wimmer |

| | | | |
|---|---|---|---|
| 6,761,685 B2 | 7/2004 | Adams et al. | |
| 6,783,491 B2 | 8/2004 | Saadat et al. | |
| 6,790,173 B2 | 9/2004 | Saadat et al. | |
| 6,800,056 B2 | 10/2004 | Tartaglia et al. | |
| 2001/0000040 A1 | 3/2001 | Adams et al. | |
| 2002/0022765 A1 | 2/2002 | Belson | |
| 2002/0062062 A1 | 5/2002 | Belson | |
| 2002/0120178 A1 | 8/2002 | Targaglia | |
| 2002/0147385 A1 | 10/2002 | Butler et al. | |
| 2002/0161281 A1 | 10/2002 | Jaffe | |
| 2002/0193661 A1 | 12/2002 | Belson | |
| 2002/0193662 A1 | 12/2002 | Belson | |
| 2003/0045778 A1 | 3/2003 | Ohline | |
| 2003/0083550 A1 | 5/2003 | Miyagi | |
| 2003/0130598 A1 | 7/2003 | Manning et al. | |
| 2003/0149338 A1 | 8/2003 | Francois et al. | |
| 2003/0195387 A1 | 10/2003 | Kortenbch et al. | |
| 2003/0233027 A1 | 12/2003 | Ewers et al. | |
| 2003/0233056 A1 | 12/2003 | Saadat et al. | |
| 2003/0233057 A1 | 12/2003 | Saadat et al. | |
| 2003/0233058 A1 | 12/2003 | Ewers et al. | |
| 2003/0233066 A1 | 12/2003 | Ewers et al. | |
| 2003/0236505 A1 | 12/2003 | Bonadio et al. | |
| 2003/0236549 A1 | 12/2003 | Bonadio et al. | |
| 2004/0044270 A1 | 3/2004 | Barry | |
| 2004/0106852 A1 | 6/2004 | Windheuser et al. | |
| 2004/0193008 A1 | 9/2004 | Jaffe et al. | |
| 2004/0193009 A1 | 9/2004 | Jaffe et al. | |
| 2005/0085693 A1 | 4/2005 | Belson et al. | |

FOREIGN PATENT DOCUMENTS

| | | | |
|---|---|---|---|
| DE | 3707787 A1 | 9/1988 | |
| EP | 0497781 B1 | 1/1994 | |
| FR | 2732225 A1 | 10/1996 | |
| JP | 63-136014 | 8/1988 | |
| WO | WO 93/17751 A1 | 3/1993 | |
| WO | WO 94/19051 A1 | 9/1994 | |
| WO | WO 95/04556 A2 | 2/1995 | |
| WO | WO 97/10746 A1 | 3/1997 | |
| WO | WO 99/33392 A1 | 7/1999 | |
| WO | WO 99/51283 A2 | 10/1999 | |
| WO | WO 99/59664 A1 | 11/1999 | |
| WO | WO 00/54653 A1 | 9/2000 | |
| WO | WO 01/49353 A2 | 7/2001 | |
| WO | WO 01/67964 A2 | 9/2001 | |
| WO | WO 01/70096 A1 | 9/2001 | |
| WO | WO 01/70097 A1 | 9/2001 | |
| WO | WO 01/74235 A1 | 10/2001 | |
| WO | WO 01/80935 A1 | 11/2001 | |
| WO | WO 02/24058 A2 | 3/2002 | |
| WO | WO 02/39909 | 5/2002 | |
| WO | WO 02/064028 A1 | 8/2002 | |
| WO | WO 02/068988 A1 | 9/2002 | |
| WO | WO 02/069841 A2 | 9/2002 | |
| WO | WO 02/096276 A1 | 12/2002 | |
| WO | WO 03/028547 A2 | 4/2003 | |
| WO | WO 03/092476 A2 | 11/2003 | |
| WO | WO 2004/006980 A2 | 1/2004 | |
| WO | WO 2004/049905 A2 | 6/2004 | |
| WO | WO 2004/071284 A1 | 8/2004 | |
| WO | WO 2004/080313 A1 | 9/2004 | |
| WO | WO 2004/084702 A2 | 10/2004 | |

OTHER PUBLICATIONS

Lee, T.S. et al., "A highly redundant robot system for inspection", Proceedings of Conference on Intelligent Robotics in Field, Factory, Service, and Space (CIRFFSS '94), (Mar. 21-24, 1994), 1:142-148, Houston, Texas.

McKernan, J.B. et al., "Laparoscopic general surgery", *Journal of the Medical Association of Georgia*, (Mar. 1990), 79(3):157-159.

Slatkin, A.B. et al., "The development of a robotic endoscope", Proceedings 1995 IEEE/RSJ International Conference on Intelligent Robots and Systems, (Aug. 5-9, 1995), 2:162-171, Pittsburgh, Pennsylvania.

Science & Technology, *Laptop Magazine*, (Oct. 2002) p. 98.

* cited by examiner

STEERABLE ENDOSCOPE AND IMPROVED METHOD OF INSERTION

CROSS-REFERENCE TO OTHER APPLICATIONS

The present application is a continuation of U.S. patent application Ser. No. 10/229,189, filed Aug. 26, 2002 now U.S. Pat. No. 7,044,907, which is a continuation of U.S. patent application Ser. No. 09/790,204, filed Feb. 20, 2001, now U.S. Pat. No. 6,468,203, which claims priority of U.S. Provisional Patent Application Ser. No. 60/194,140, filed Apr. 3, 2000, each of the above applications is incorporated herein by reference for all purposes.

FIELD OF THE INVENTION

The present invention relates generally to endoscopes and endoscopic medical procedures. More particularly, it relates to a method and apparatus to facilitate insertion of a flexible endoscope along a tortuous path, such as for colonoscopic examination and treatment.

BACKGROUND OF THE INVENTION

An endoscope is a medical instrument for visualizing the interior of a patient's body. Endoscopes can be used for a variety of different diagnostic and interventional procedures, including colonoscopy, bronchoscopy, thoracoscopy, laparoscopy and video endoscopy.

Colonoscopy is a medical procedure in which a flexible endoscope, or colonoscope, is inserted into a patient's colon for diagnostic examination and/or surgical treatment of the colon. A standard colonoscope is typically 135-185 cm in length and 12-13 mm in diameter, and includes a fiberoptic imaging bundle, illumination fibers and one or two instrument channels that may also be used for insufflation or irrigation. The colonoscope is inserted via the patient's anus and is advanced through the colon, allowing direct visual examination of the colon, the ileocecal valve and portions of the terminal ileum. Insertion of the colonoscope is complicated by the fact that the colon represents a tortuous and convoluted path. Considerable manipulation of the colonoscope is often necessary to advance the colonoscope through the colon, making the procedure more difficult and time consuming and adding to the potential for complications, such as intestinal perforation. Steerable colonoscopes have been devised to facilitate selection of the correct path though the curves of the colon. However, as the colonoscope is inserted farther and farther into the colon, it becomes more difficult to advance the colonoscope along the selected path. At each turn, the wall of the colon Must maintain the curve in the colonoscope. The colonoscope rubs against the mucosal surface of the colon along the outside of each turn. Friction and slack in the colonoscope build up at each turn, making it more and more difficult to advance and withdraw the colonoscope. In addition, the force against the wall of the colon increases with the buildup of friction. In cases of extreme tortuosity, it may become impossible to advance the colonoscope all of the way through the colon.

Steerable endoscopes, catheters and insertion devices for medical examination or treatment of internal body structures are described in the following U.S. patents, the disclosures of which are hereby incorporated by reference in their entirety: U.S. Pat. Nos. 4,753,223; 5,337,732; 5,662,587; 4,543,090; 5,383,852; 5,487,757 and 5,337,733.

SUMMARY OF THE INVENTION

In keeping with the foregoing discussion, the present invention takes the form of a steerable endoscope for negotiating tortuous paths through a patient's body. The steerable endoscope can be used for a variety of different diagnostic and interventional procedures, including colonoscopy, bronchoscopy, thoracoscopy, laparoscopy and video endoscopy. The steerable endoscope is particularly well suited for negotiating the tortuous curves encountered when performing a colonoscopy procedure.

The steerable endoscope has an elongated body with a manually or selectively steerable distal portion and an automatically controlled proximal portion. The selectively steerable distal portion can be selectively steered or bent up to a full 180 degree bend in any direction. A fiberoptic imaging bundle and one or more illumination fibers extend through the body from the proximal end to the distal end. Alternatively, the endoscope can be configured as a video endoscope with a miniaturized video camera, such as a CCD camera, which transmits images to a video monitor by a transmission cable or by wireless transmission. Optionally, the endoscope may include one or two instrument channels that may also be used for insufflation or irrigation.

A proximal handle attached to the elongate body includes an ocular for direct viewing and/or for connection to a video camera, a connection to an illumination source and one or more luer lock fittings that are connected to the instrument channels. The handle is connected to a steering control for selectively steering or bending the selectively steerable distal portion in the desired direction and to an electronic motion controller for controlling the automatically controlled proximal portion of the endoscope. An axial motion transducer is provided to measure the axial motion of the endoscope body as it is advanced and withdrawn. Optionally, the endoscope may include a motor or linear actuator for automatically advancing and withdrawing the endoscope.

The method of the present invention involves inserting the distal end of the endoscope body into a patient, either through a natural orifice or through an incision, and steering the selectively steerable distal portion to select a desired path. When the endoscope body is advanced, the electronic motion controller operates the automatically controlled proximal portion of the body to assume the selected curve of the selectively steerable distal portion. This process i repeated by selecting another desired path with the selectively steerable distal portion and advancing the endoscope body again. As the endoscope body is further advanced, the selected curves propagate proximally along the endoscope body. Similarly, when the endoscope body is withdrawn proximally, the selected curves propagate distally along the endoscope body. This creates a sort of serpentine motion in the endoscope body that allows it to negotiate tortuous curves along a desired path through or around and between organs within the body.

The method can be used for performing colonoscopy or other endoscopic procedures, such as bronchoscopy, thoracoscopy, laparoscopy and video endoscopy. In addition, the apparatus and methods of the present invention can be used for inserting other types of instruments, such as surgical instruments, catheters or introducers, along a desired path within the body.

DETAILED DESCRIPTION OF THE INVENTION

Figure 1:
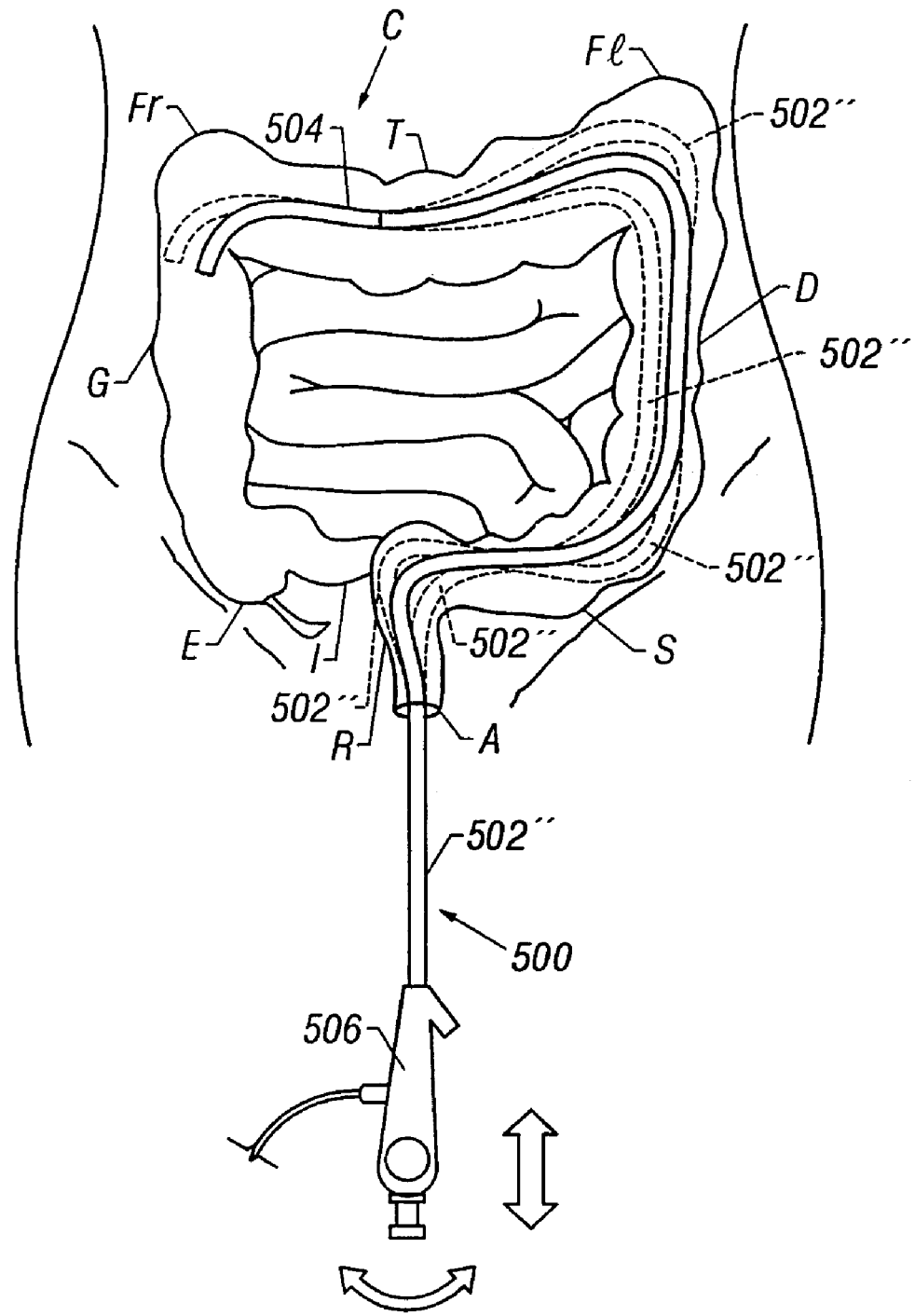
FIG. 1 shows a prior art colonoscope being employed for a colonoscopic examination of a patient's colon.

FIG. 1 shows a prior art colonoscope 500 being employed for a colonoscopic examination of a patient's colon C. The colonoscope 500 has a proximal handle 506 and an elongate body 502 with a steerable distal portion 504. The body 502 of the colonoscope 500 has been lubricated and inserted into the colon C via the patient's anus A. Utilizing the steerable distal portion 504 for guidance, the body 502 of the colonoscope 500 has been maneuvered through several turns in the patient's colon C to the ascending colon G. Typically, this involves a considerable amount of manipulation by pushing, pulling and rotating the colonoscope 500 from the proximal end to advance it through the turns of the colon C. After the steerable distal portion 504 has passed, the wall of the colon C maintains the curve in the flexible body 502 of the colonoscope 500 as it is advanced. Friction develops along the body 502 of the colonoscope 500 as it is inserted, particularly at each turn in the colon C. Because of the friction, when the user attempts to advance the colonoscope 500, the body 502' tends to move outward at each curve, pushing against the wall of the colon C, which exacerbates the problem by increasing the friction and making it more difficult to advance the colonoscope 500. On the other hand, when the colonoscope 500 is withdrawn, the body 502" tends to move inward at each curve taking up the slack that developed when the colonoscope 500 was advanced. When the patient's colon C is extremely tortuous, the distal end of the body 502 becomes unresponsive to the user's manipulations, and eventually it may become impossible to advance the colonoscope 500 any farther. In addition to the difficulty that it presents to the user, tortuosity of the patient's colon also increases the risk of complications, such as intestinal perforation.

Figure 2:
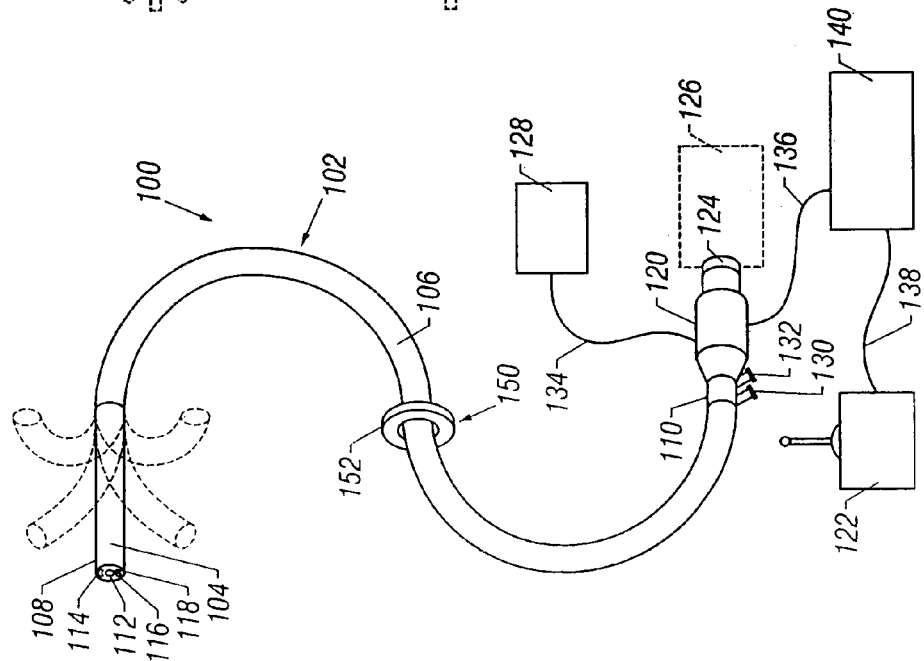
FIG. 2 shows a first embodiment of the steerable endoscope of the present invention.

FIG. 2 shows a first embodiment of the steerable endoscope 100 of the present invention. The endoscope 100 has an elongate body 102 with a manually or selectively steerable distal portion 104 and an automatically controlled proximal portion 106. The selectively steerable distal portion 104 can be selectively steered or bent up to a full 180 degree bend in any direction. A fiberoptic imaging bundle 112 and one or more illumination fibers 114 extend through the body 102 from the proximal end 110 to the distal end 108. Alternatively, the endoscope 100 can be configured as a video endoscope with a miniaturized video camera, such as a CCD camera, positioned at the distal end 108 of the endoscope body 102. The images from the video camera can be transmitted to a video monitor by a transmission cable or by wireless transmission. Optionally, the body 102 of the endoscope 100 may include one or two instrument channels 116, 118 that may also be used for insufflation or irrigation. The body 102 of the endoscope 100 is highly flexible so that it is able to bend around small diameter curves without buckling or kinking. When configured for use as a colonoscope, the body 102 of the endoscope 100 is typically from 135 to 185 cm in length and approximately 12-13 mm in diameter. The endoscope 100 can be made in a variety of other sizes and configurations for other medical and industrial applications.

A proximal handle 120 is attached to the proximal end 110 of the elongate body 102. The handle 120 includes an ocular 124 connected to the fiberoptic imaging bundle 112 for direct viewing and/or for connection to a video camera 126. The handle 120 is connected to an illumination source 128 by an illumination cable 134 that is connected to or continuous with the illumination fibers 114. A first luer lock fitting, 130 and a second luer lock fitting 132 on the handle 120 are connected to the instrument channels 116, 118.

The handle 120 is connected to an electronic motion controller 140 by way of a controller cable 136. A steering control 122 is connected to the electronic motion controller 140 by way of a second cable 13 M. The steering control 122 allows the user to selectively steer or bend the selectively steerable distal portion 104 of the body 102 in the desired direction. The steering control 122 may be a joystick controller as shown, or other known steering control mechanism. The electronic motion controller 140 controls the motion of the automatically controlled proximal portion 106 of the body 102. The electronic motion controller 140 may be implemented using a motion control program running on a microcomputer or using an application-specific motion controller. Alternatively, the electronic motion controller 140 may be implemented using, a neural network controller.

An axial motion transducer 150 is provided to measure the axial motion of the endoscope body 102 as it is advanced and withdrawn. The axial motion transducer 150 can be made in many possible configurations. By way of example, the axial motion transducer 150 in FIG. 2 is configured as a ring 152 that surrounds the body 102 of the endoscope 100. The axial motion transducer 150 is attached to a fixed point of reference, such as the surgical table or the insertion point for the endoscope 100 on the patient's body. As the body 102 of the endoscope 100 slides through the axial motion transducer 150, it produces a signal indicative of the axial position of the endoscope body 102 with respect to the fixed point of reference and sends a signal to the electronic motion controller 140 by telemetry or by a cable (not shown). The axial motion transducer 150 may use optical, electronic or mechanical means to measure the axial position of the endoscope body 102. Other possible configurations for the axial motion transducer 150 are described below.

Figure 3:
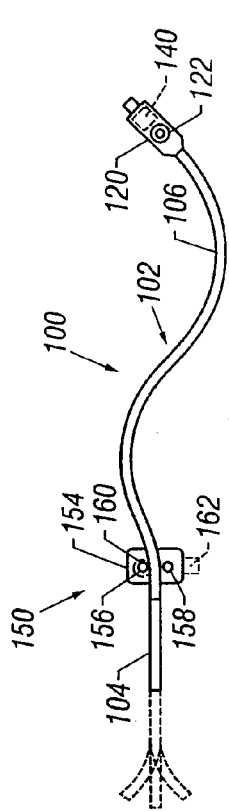
FIG. 3 shows a second embodiment of the steerable endoscope of the present invention.

FIG. 3 shows a second embodiment of the endoscope 100 of the present invention. As in the embodiment of FIG. 2, the endoscope 100 has an elongate body 102 with a selectively steerable distal portion 104 and an automatically controlled proximal portion 106. The steering control 122 is integrated into proximal handle 120 in the form or one or two dials for selectively steering, the selectively steerable distal portion 104 of the endoscope 100. Optionally, the electronic motion controller 140 may be miniaturized and integrated into proximal handle 120, as well. In this embodiment, the axial motion transducer 150 is configured with a base 154 that is attachable to a fixed point of reference, such as the surgical table. A first roller 156 and a second roller 158 contact the exterior of the endoscope body 102. A multi-turn potentiometer 160 or other motion transducer is connected to the first roller 156 to measure the axial motion of the endoscope body 102 and to produce a signal indicative of the axial position.

The endoscope 100 may be manually advanced or withdrawn by the user by grasping the body 102 distal to the axial motion transducer 150. Alternatively, the first roller 156 and/or second roller 158 may be connected to a motor 162 for automatically advancing and withdrawing the body 102 of the endoscope 100.

Figure 4:
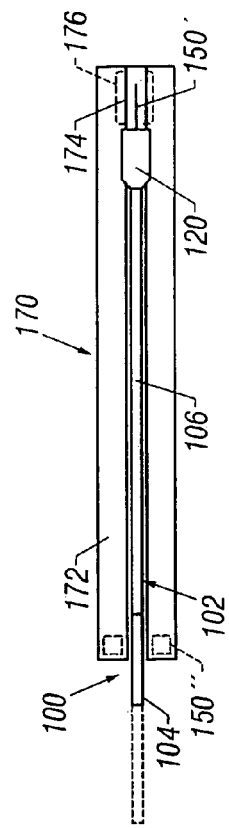
FIG. 4 shows a third embodiment of the steerable endoscope of the present invention.

FIG. 4 shows a third embodiment of the endoscope 100 of the present invention, which utilizes an elongated housing 170 to organize and contain the endoscope 100. The housing 170 has a base 172 with a linear track 174 to guide the body 102 of the endoscope 100. The housing 170 may have an axial motion transducer 150' that is configured as a linear motion transducer integrated into the linear track 174. Alternatively, the housing, 170 may have an axial motion transducer 150" configured similarly to the axial motion transducer 150 in FIG. 2 or 3. The endoscope 100 may be manually advanced or withdrawn by the user by grasping the body 102 distal to the housing 170. Alternatively, the housing 170 may include a motor 176 or other linear motion actuator for automatically advancing and withdrawing the body 102 of the endoscope 100. In another alternative configuration, a motor with friction wheels, similar to that described above in connection with FIG. 3, may be integrated into the axial motion transducer 150".

Figure 5:
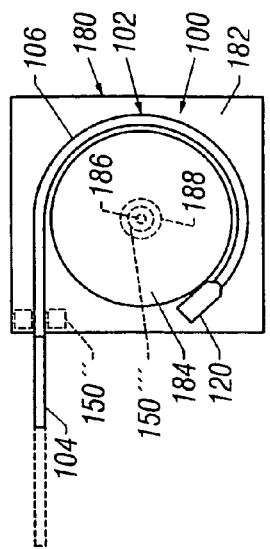
FIG. 5 shows a fourth embodiment of the steerable endoscope of the present invention.

FIG. 5 shows a fourth embodiment of the endoscope 100 of the present invention, which utilizes a rotary housing 180 to organize and contain the endoscope 100. The housing 180 has a base 182 with a rotating drum 184 to guide the body 102 of the endoscope 100. The housing 180 may have an axial motion transducer 150''' that is configured as a potentiometer connected to the pivot axis 186 of the rotating drum 184. Alternatively, the housing 180 may have an axial motion transducer 150" configured similarly to the axial motion transducer 150 in FIG. 2 or 3. The endoscope 100 may be manually advanced or withdrawn by the user by grasping the body 102 distal to the housing 180. Alternatively, the housing 180 may include a motor 188 connected to the rotating drum 184 for automatically advancing and withdrawing the body 102 of the endoscope 100. In another alternative configuration, a motor with friction wheels, similar to that described above in connection with FIG. 3, may be integrated into the axial motion transducer 150".

Figure 6:
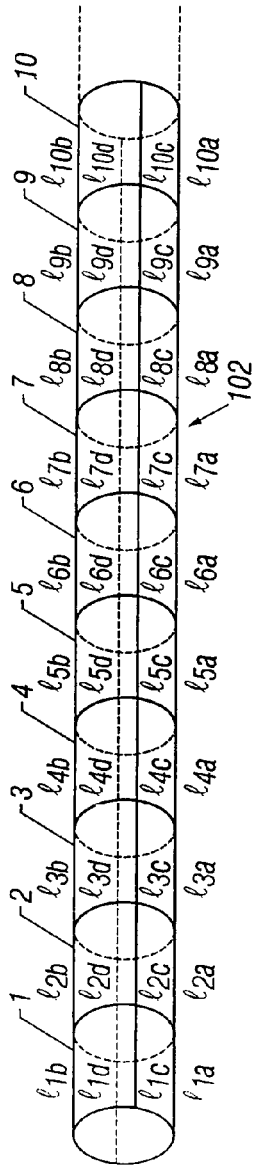
FIG. 6 shows a wire frame model of a section of the body of the endoscope in a neutral or straight position.

FIG. 6 shows a wire frame model of a section of the body 102 of the endoscope 100 in a neutral or straight position. Most of the internal structure of the endoscope body 102 has been eliminated in this drawing for the sake of clarity. The endoscope body 102 is divided up into sections 1, 2, 3 . . . 10, etc. The geometry of each section is defined by four length measurements along the a, b, c and d axes. For example, the geometry of section 1 is defined by the four length measurements $l_{1a}, l_{1b}, l_{1c}, l_{1d}$, and the geometry of section 2 is defined by the four length measurements $l_{2a}, l_{2b}, l_{2c}, l_{2d}$, etc. Preferably, each of the length measurements is individually controlled by a linear actuator (not shown). The linear actuators may utilize one of several different operating principles. For example, each of the linear actuators may be a self-heating NiTi alloy linear actuator or an electrorheological plastic actuator, or other known mechanical, pneumatic, hydraulic or electromechanical actuator. The geometry of each section may be altered using the linear actuators to change the four length measurements along the a, b, c and d axes. Preferably, the length measurements are changed in complementary pairs to selectively bend the endoscope body 102 in a desired direction. For example, to bend the endoscope body 102 in the direction of the a axis, the measurements $l_{1a}, l_{2a}, l_{3a} \ldots l_{10a}$ would be shortened and the measurements $l_{1b}, l_{2b}, l_{3b} \ldots l_{10b}$ would be lengthened an equal amount. The amount by which these measurements are changed determines the radius of the resultant curve.

In the selectively steerable distal portion 104 of the endoscope body 102, the linear actuators that control the a, b, c and d axis measurements of each section are selectively controlled by the user through the steering control 122. Thus, by appropriate control of the a, b, c and d axis measurements, the selectively steerable distal portion 104 of the endoscope body 102 can be selectively steered or bent up to a full 180 degrees in any direction.

Figure 7:
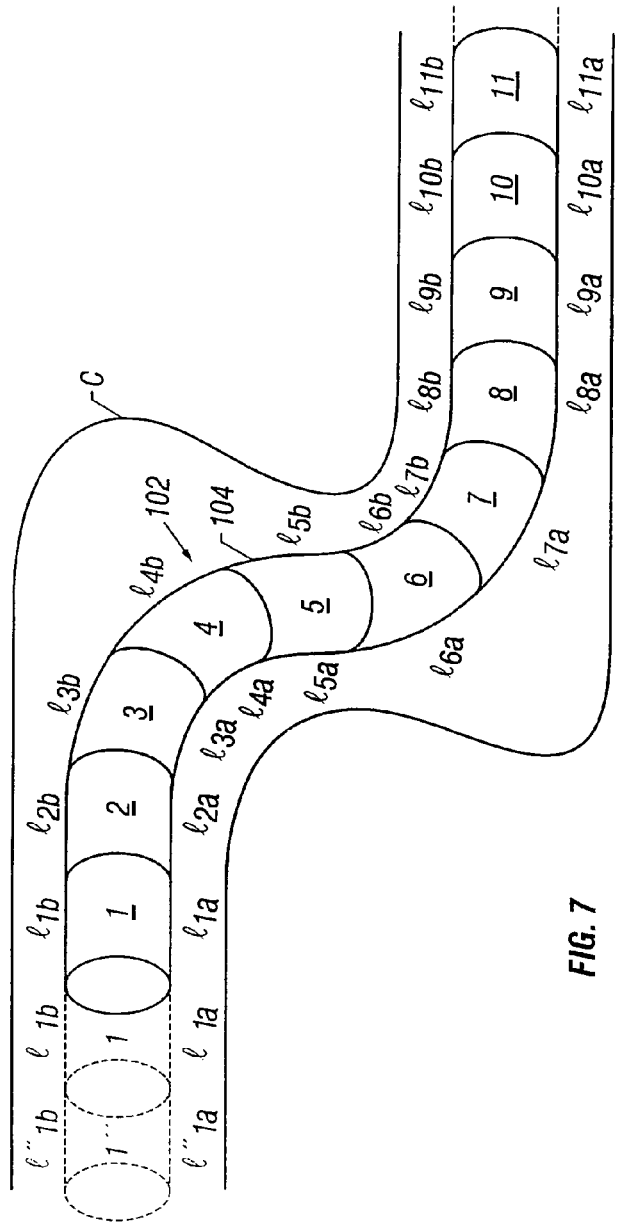
FIG. 7 shows the wire frame model of the endoscope body shown in FIG. 6 passing through a curve in a patient's colon.

In the automatically controlled proximal portion 106, however, the a, b, c and d axis measurements of each section are automatically controlled by the electronic motion controller 140, which uses a curve propagation method to control the shape of the endoscope body 102. To explain how the curve propagation method operates, FIG. 7 shows the wire frame model of a part of the automatically controlled proximal portion 106 of the endoscope body 102 shown in FIG. 6 passing, through a curve in a patient's colon C. For simplicity, an example of a two-dimensional curve is shown and only the a and b axes will be considered. In a three-dimensional curve all four of the a, b, c and d axes would be brought into play.

In FIG. 7, the endoscope body 102 has been maneuvered through the curve in the colon C with the benefit of the selectively steerable distal portion 104 (this part of the procedure is explained in more detail below) and now the automatically controlled proximal portion 106 resides in the curve. Sections 1 and 2 are in a relatively straight part of the colon C, therefore $l_{1a}=l_{1b}$ and $l_{2a}=l_{2b}$. However, because sections 3-7 are in the S-shaped curved section, $l_{3a}<l_{3b}$, $l_{4a}<l_{4b}$ and $l_{5a}<l_{5b}$, but $l_{6a}>l_{6b}$, $l_{7a}>l_{7b}$ and $l_{8a}>l_{8b}$. When the endoscope body 102 is advanced distally by one unit, section 1 moves into the position marked 1', section 2 moves into the position previously occupied by section 1, section 3 moves into the position previously occupied by section 2, etc. The axial motion transducer 150 produces a signal indicative of the axial position of the endoscope body 102 with respect to a fixed point of reference and sends the signal to the electronic motion controller 140, Under control of the electronic motion controller 140, each time the endoscope body 102 advances one unit, each section in the automatically controlled proximal portion 106 is signaled to assume the shape of the section that previously occupied the space that it is now in. Therefore, when the endoscope body 102 is advanced to the position marked 1', $l_{1a}=l_{1b}$, $l_{2a}=l_{2b}$, $l_{3a}=l_{3b}$, $l_{4a}<l_{4b}$, $l_{5a}<l_{5b}$, $l_{6a}<l_{6b}$, $l_{7a}>l_{7b}$ and $l_{8a}>l_{8b}$, and $l_{9a}>l_{9b}$, when the endoscope body 102 is advanced to the position marked 1", $l_{1a}=l_{1b}$, $l_{2a}=l_{2}$, $l_{3a}=l_{3b}$, $l_{4a}=l_{4b}$, $l_{5a}<l_{5b}$, $l_{6a}<l_{6b}$, $l_{7a}<l_{7b}$, $l_{8a}>l_{8b}$, $l_{9a}>l_{9b}$, and $l_{10a}>l_{10b}$. Thus, the S-shaped curve propagates proximally along the length of the automatically controlled proximal portion 106 of the endoscope body 102. The S-shaped curve appears to be fixed in space, as the endoscope body 102 advances distally.

Similarly, when the endoscope body 102 is withdrawn proximally, each time the endoscope body 102 is moved proximally by one unit, each section in the automatically controlled proximal portion 106 is signaled to assume the shape of the section that previously occupied the space that it is now in. The S-shaped curve propagates distally along the length of the automatically controlled proximal portion 106 of the endoscope body 102, and the S-shaped curve appears to be fixed in space, as the endoscope body 102 withdraws proximally.

Whenever the endoscope body 102 is advanced or withdrawn, the axial motion transducer 150 detects the change in position and the electronic motion controller 140 propagates the selected curves proximally or distally along the automatically controlled proximal portion 106 of the endoscope body 102 to maintain the curves in a spatially fixed position. This allows the endoscope body 102 to move through tortuous curves without putting unnecessary force on the wall of the colon C.

Figure 8:
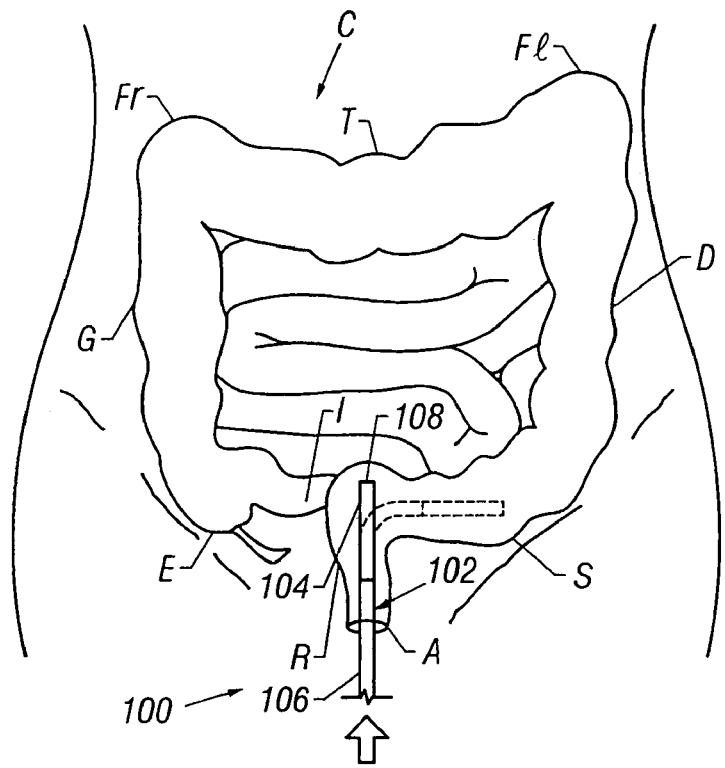
FIGS. 8-13 show the endoscope of the present invention being employed for a colonoscopic examination of a patient's colon.

FIGS. 8-13 show the endoscope 100 of the present invention being employed for a colonoscopic examination of a patient's colon. In FIG. 8, the endoscope body 102 has been lubricated and inserted into the patient's colon C through the anus A. The distal end 108 of the endoscope body 102 is advanced through the rectum R until the first turn in the colon C is reached, as observed through the ocular 124 or on a video monitor. To negotiate the turn, the selectively steerable distal portion 104 of the endoscope body 102 is manually steered toward the sigmoid colon S by the user through the steering control 122. The control signals from the steering control 122 to the selectively steerable distal portion 104 are monitored b the electronic y motion controller 140. When the correct curve of the selectively steerable distal portion 104 for advancing the distal end 108 of the endoscope body 102 into the sigmoid colon S has been selected, the curve is logged into the memory of the electronic motion controller 140 as a reference. This step can be performed in a manual mode, in which the user gives a command to the electronic motion controller 140 to record the selected curve, using keyboard commands or voice commands. Alternatively, this step can be performed in an automatic mode, in which the user signals to the electronic motion controller 140 that the desired curve has been selected by advancing the endoscope body 102 distally.

Whether operated in manual mode or automatic mode, once the desired curve has been selected with the selectively steerable distal portion 104, the endoscope body 102 is advanced distally and the selected curve is propagated proximally along the automatically controlled proximal portion 106 of the endoscope body 102 by the electronic motion controller 140, as described above. The curve remains fixed in space while the endoscope body 102 is advanced distally through the sigmoid colon S. In a particularly tortuous colon, the selectively steerable distal portion 104 may have to be steered through multiple curves to traverse the sigmoid colon S.

Figure 9:
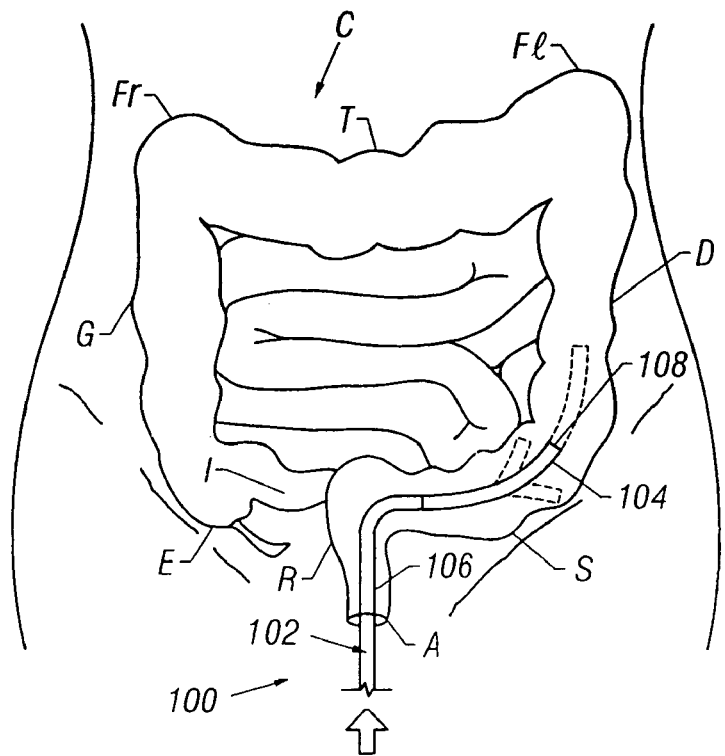
Figure 10:
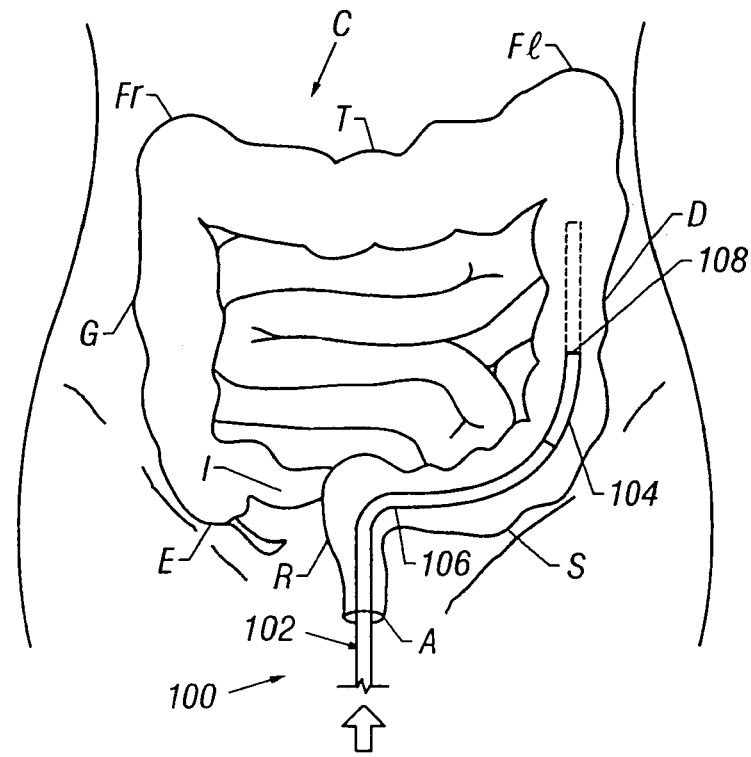

As illustrated in FIG. 9, the user may stop the endoscope 100 at any point for examination or treatment of the mucosal surface or any other features within the colon C. The selectively steerable distal portion 104 may be steered in any direction to examine the inside of the colon C. When the user has completed the examination of the sigmoid colon S, the selectively steerable distal portion 104 is steered in a superior direction toward the descending colon D. Once the desired curve has been selected with the selectively steerable distal portion 104, the endoscope body 102 is advanced distally into the descending colon D, and the second curve as well as the first curve are propagated proximally along the automatically controlled proximal portion 106 of the endoscope body 102, as shown in FIG. 10.

If, at any time, the user decides that the path taken by the endoscope body 102 needs to be revised or corrected, the endoscope 100 may be withdrawn proximally and the electronic motion controller 140 commanded to erase the previously selected curve. This can be done manually using keyboard commands or voice commands or automatically by programming the electronic motion controller 140 to go into a revise mode when the endoscope body 102 is withdrawn a certain distance. The revised or corrected curve is selected using the selectively steerable distal portion 104, and the endoscope body 102 is advanced as described before.

Figure 11:
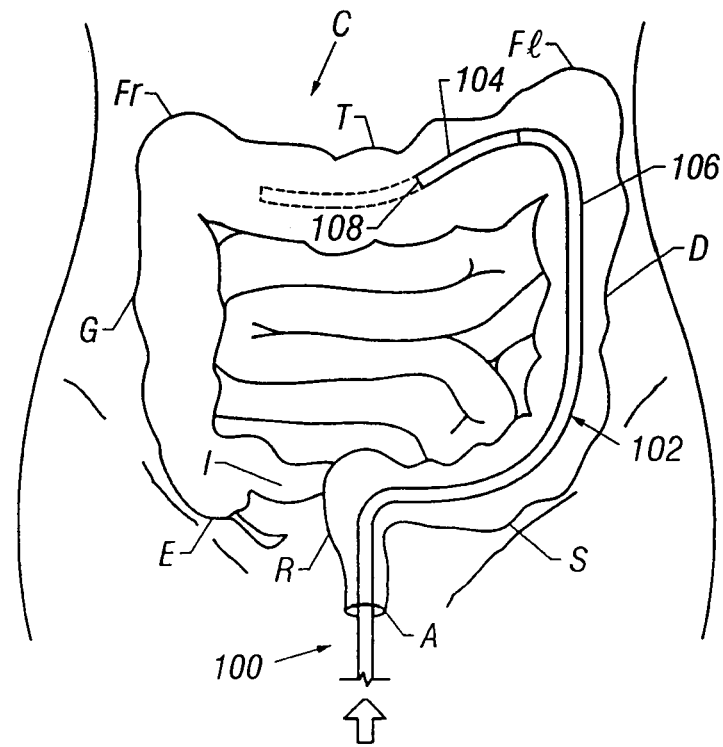
Figure 12:
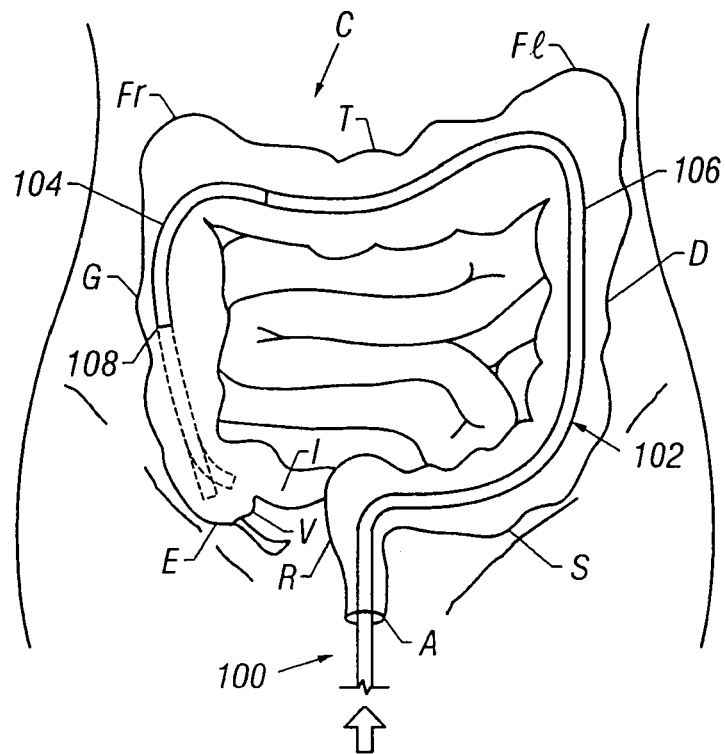

The endoscope body 102 is advanced through the descending colon D until it reaches the left (splenic) flexure $F_l$ of the colon. Here, in many cases, the endoscope body 102 must negotiate an almost 180 degree hairpin turn. As before, the desired curve is selected using the selectively steerable distal portion 104, and the endoscope body 102 is advanced distally through the transverse colon T, as shown in FIG. 11. Each of the previously selected curves is propagated proximally along the automatically controlled proximal portion 106 of the endoscope body 102. The same procedure is followed at the right (hepatic) flexure Fr of the colon and the distal end 108 of the endoscope body 102 is advanced through the ascending colon G to the cecum E, as shown in FIG. 12. The cecum E, the ileocecal valve V and the terminal portion of the ileum I can be examined from this point using, the selectively steerable distal portion 104 of the endoscope body 102.

Figure 13:
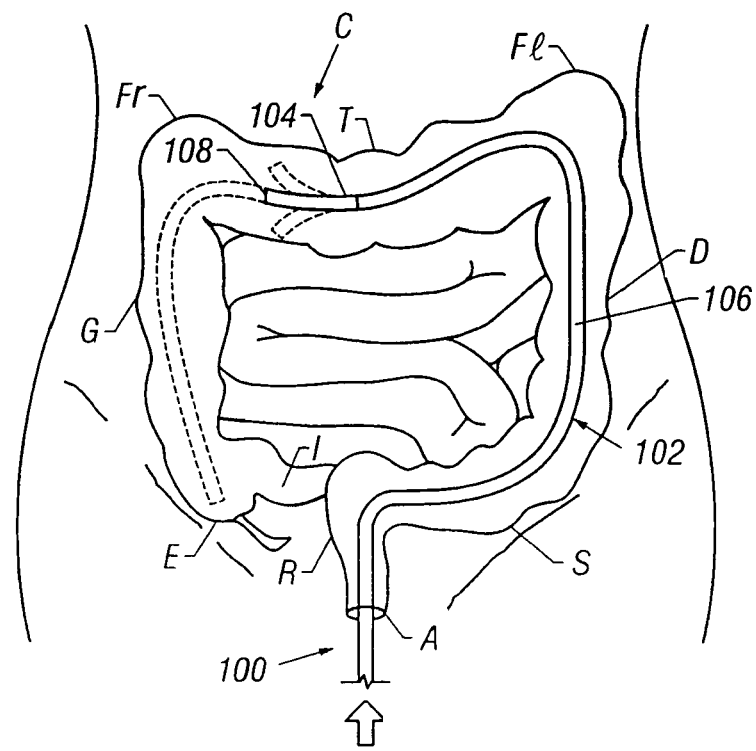

FIG. 13 shows the endoscope 100 being, withdrawn through the colon C. As the endoscope 100 is withdrawn, the endoscope body 102 follows the previously selected curves by propagating the curves distally along the automatically controlled proximal portion 106, as described above. At any point, the user may stop the endoscope 100 for examination or treatment of the mucosal surface or any other features within the colon C using the selectively steerable distal portion 104 of the endoscope body 102.

In one preferred method according to the present invention, the electronic motion controller 140 includes an electronic memory in which is created a three-dimensional mathematical model of the patient's colon or other anatomy through which the endoscope body 102 is maneuvered. The three-dimensional model can be annotated by the operator to record the location of anatomical landmarks, lesions, polyps, biopsy samples and other features of interest. The three-dimensional model of the patient's anatomy can be used to facilitate reinsertion of the endoscope body 102 in subsequent procedures. In addition, the annotations can be used to quickly find the location of the features of interest. For example, the three-dimensional model can be annotated with the location where a biopsy sample was taken during an exploratory endoscopy. The site of the biopsy sample can be reliably located again in follow-up procedures to track the progress of a potential disease process and/or to perform a therapeutic procedure at the site.

In one particularly preferred variation of this method, the electronic motion controller 140 can be programmed, based on the three-dimensional model in the electronic memory, so that the endoscope body 102 will automatically assume the proper shape to follow the desired path as it is advanced through the patient's anatomy. In embodiments of the steerable endoscope 100 that are configured for automatically advancing and withdrawing the endoscope body 102, as described above in connection with FIGS. 3, 4 and 5, the endoscope body 102 can be commanded to advance automatically though the patient's anatomy to the site of a previously noted lesion or other point of interest based on the three-dimensional model in the electronic memory.

Imaging software would allow the three-dimensional model of the patient's anatomy obtained using the steerable endoscope 100 to be viewed on a computer monitor or the like. This would facilitate comparisons between the three-dimensional model and images obtained with other imaging modalities, for example fluoroscopy, radiography, ultrasonography, magnetic resonance imaging (MRI), computed tomography (CT scan), electron beam tomography or virtual colonoscopy. Conversely, images from these other imaging modalities can be used to map out an approximate path or trajectory to facilitate insertion of the endoscope body 102. In addition, images from other imaging modalities can be used to facilitate locating suspected lesions with the steerable endoscope 100. For example, images obtained using a barium-contrast radiograph of the colon can be used to map out an approximate path to facilitate insertion of the endoscope body 102 into the patient's colon. The location and depth of any suspected lesions seen on the radiograph can be noted so that the endoscope body 102 can be quickly and reliably guided to the vicinity of the lesion.

Imaging modalities that provide three-dimensional information, such as biplanar fluoroscopy, CT or MRI, can be used to program the electronic motion controller 140 so that the endoscope body 102 will automatically assume the proper shape to follow the desired path as it is advanced through the patient's anatomy. In embodiments of the steerable endoscope 100 that are configured for automatically advancing and withdrawing the endoscope body 102, the endoscope body 102 can be commanded to advance automatically though the patient's anatomy along the desired path as determined by the three-dimensional imacrinc, information. Similarly, the endoscope body 102 can be commanded to advance automatically to the site of a suspected lesion or other point of interest noted on the images.

Although the endoscope of the present invention has been described for use as a colonoscope, the endoscope can be configured for a number of other medical and industrial applications. In addition, the present invention can also be configured as a catheter, cannula, surgical instrument or introducer sheath that uses the principles of the invention for navigating through tortuous body channels.

In a variation of the method that is particularly applicable to laparoscopy or thoracoscopy procedures, the steerable endoscope 100 can be selectively maneuvered along a desired path around and between organs in a patient's body cavity. The distal end 108 of the endoscope 100 is g inserted into the patient's body cavity through a natural opening, through a surgical incision or through a surgical cannula or introducer. The selectively steerable distal portion 104 can be used to explore and examine the patient's body cavity and to select a path around and between the patient's organs. The electronic motion controller 140 can be used to control the automatic ally controlled proximal portion 106 of the endoscope body 102 to follow the selected path and, if necessary, to return to a desired location using the three-dimensional model in the electronic memory of the electronic motion controller 140.

While the present invention has been described herein with respect to the exemplary embodiments and the best mode for practicing the invention, it will be apparent to one of ordinary skill in the art that man modifications, improvements and subcombinations of the various embodiments, adaptations and variations can be made to the invention without departing from the spirit and scope thereof.

I claim:

1. A method of advancing an instrument along a path, comprising: selectively steering a distal portion of the instrument to assume a selected curve along the path; and creating a three dimensional model of the selected curve in the memory of an electronic motion controller.

2. The method according to claim 1, further comprising: programming the electronic motion controller based on the created three dimensional model so that the instrument will automatically assume the proper shape to follow the selected curve as the instrument is advanced along the path.

3. The method according to claim 1, further comprising: programming the electronic motion controller based on the created three dimensional model.

4. The method according to claim 1, further comprising: advancing the instrument distally while automatically controlling a proximal portion of the instrument using the electronic motion controller to propagate the selected curve distally along the proximal portion of the instrument.

5. The method according to claim 3, further comprising: advancing the instrument proximally while automatically controlling a proximal portion of the instrument using the electronic motion controller to propagate the selected curve proximally along the proximal portion of the instrument.

6. The method according to claim 3, further comprising: modifying the programming of the electronic motion controller by withdrawing the instrument proximally and commanding the electronic motion controller to erase the selected curve.

7. The method according to claim 3 wherein the electronic motion controller receives an input from an axial motion transducer indicative of the axial position of the instrument.

8. The method according to claim 1 wherein the electronic motion controller receives a signal from an axial motion transducer indicative of the axial position of the instrument.

9. A method of advancing an instrument along a path, comprising: attempting more than one time to selectively steer the distal portion of the instrument along the path; selecting a curve from the attempts to selectively steer the distal portion of the instrument along the path; and logging the curve into the memory of an electronic motion controller adapted to control the instrument.

10. The method according to claim 9 further comprising: automatically controlling the proximal portion of the instrument to propagate the curve along the instrument.

11. An apparatus, comprising: an elongated instrument body having a selectively steerable distal portion and an automatically controllable proximal portion, the selectively steerable distal portion being configured to selectively assume a selected curve along a desired path, and the automatically controllable proximal portion being configured to propagate the selected curve along the elongated instrument body as the elongated instrument body is advanced along the selected curve; an electronic motion controller adapted to control the instrument; an electronic memory adapted to create and store a three dimensional model of the selected curve; and a steering control connected electronic motion controller for selectively steering the instrument.

12. The apparatus according to claim 11 wherein the electronic motion controller is integrated into a proximal handle.

13. The apparatus according to claim 11 wherein the steering control is integrated into a proximal handle.

14. The apparatus according to claim 11 wherein the electronic motion controller can be programmed based on a three dimensional model stored in the electronic memory.

15. The apparatus according to claim 11 wherein the steering control comprises a joystick.

16. The apparatus according to claim 11 wherein the electronic memory is adapted to indicate and store an annotation of the three dimensional model of the selected curve.

17. The apparatus according to claim 11 further comprising a transducer for measuring motion of the elongated instrument body along the desired path.

18. The apparatus according to claim 11 wherein the selectively steerable distal portion is further adapted to be automatically controlled by the electronic motion controller.

19. The apparatus according to claim 11 wherein the elongated instrument is configured as an endoscopic instrument for insertion into a patient's body.

20. The apparatus according to claim 11 wherein the elongated instrument is configured as a surgical instrument.

* * * * *